(12) United States Patent
Ouis

(10) Patent No.: US 11,175,263 B2
(45) Date of Patent: Nov. 16, 2021

(54) APPARATUS AND METHOD FOR GENERATING, MEASURING, AND EVALUATING VIBRATIONAL MODES IN CYLINDRICAL OBJECTS

(71) Applicant: King Fahd University of Petroleum and Minerals, Dhahran (SA)

(72) Inventor: Djamel Ouis, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 130 days.

(21) Appl. No.: 16/799,125

(22) Filed: Feb. 24, 2020

(65) Prior Publication Data
US 2021/0262986 A1     Aug. 26, 2021

(51) Int. Cl.
*G01N 29/46*     (2006.01)
*G01N 33/46*     (2006.01)
(Continued)

(52) U.S. Cl.
CPC ......... *G01N 29/11* (2013.01); *G01N 29/4427* (2013.01); *G01N 29/46* (2013.01); *G01N 33/46* (2013.01)

(58) Field of Classification Search
CPC .... G01N 29/4427; G01N 29/11; G01N 33/46; G01N 29/46
(Continued)

(56) References Cited

U.S. PATENT DOCUMENTS 3,043,132 A     7/1962  Schubring
3,066,525 A     12/1962 Harris
(Continued)

FOREIGN PATENT DOCUMENTS

EP        1 070 961 A1     1/2001
JP        2009/276063      11/2009
WO        WO2017124188  *  7/2017 ............... G01N 3/30

OTHER PUBLICATIONS

OUIS ; Vibrational and acoustical experiments on logs of spruce ; Wood Science and Technology 33 ; pp. 151-184 ; Jul. 16, 1997 ; 34 Pages.
(Continued)

*Primary Examiner* — Jacques M Saint Surin
(74) *Attorney, Agent, or Firm* — Oblon, McClelland, Maier & Neustadt, L.L.P.

(57) ABSTRACT

The present disclosure relates to evaluating an ovaling mode in a cylindrical object and determining a quality of the cylindrical object by analysis of the ovaling mode. In an embodiment, the present disclosure relates to a method for determining a structural quality of a cylindrical element, comprising measuring, as a result of a single applied force, surface vibrations of the cylindrical element via four or more surface transducers arranged on the cylindrical element along a circumference of the cylindrical element, the four or more surface transducers being equally spaced along the circumference, processing digital signals corresponding to each of the four or more surface transducers in order to generate a composite digital signal, transforming the composite digital signal to a frequency domain, comparing the transformed composite digital signal to a reference composite digital signal, and determining, based on the comparing, the structural quality of the cylindrical element.

20 Claims, 12 Drawing Sheets

(51) Int. Cl.
*G01N 29/44* (2006.01)
*G01N 29/11* (2006.01)
(58) Field of Classification Search
USPC .......................................................... 73/602
See application file for complete search history.

(56) References Cited

U.S. PATENT DOCUMENTS

| | | |
|---|---|---|
| 3,345,861 A | 10/1967 | Heath |
| 3,521,483 A | 7/1970 | Miller et al. |
| 3,531,983 A | 10/1970 | Heath et al. |
| 3,641,811 A | 2/1972 | Gnaedinger, Jr. et al. |
| 3,664,180 A | 5/1972 | McDonald et al. |
| 3,877,294 A | 4/1975 | Shaw |
| 3,916,699 A | 11/1975 | Moran et al. |
| 4,059,988 A | 11/1977 | Shaw |
| 4,297,872 A | 11/1981 | Ikeda et al. |
| 4,350,044 A | 9/1982 | Richardson et al. |
| 4,399,701 A | 8/1983 | Dunlop |
| 4,702,111 A | 10/1987 | Holland |
| 4,926,691 A | 5/1990 | Franklin et al. |
| 7,971,485 B2 | 7/2011 | Greenough et al. |
| 10,933,556 B2 * | 3/2021 | Bolton .................. G06N 20/00 |
| 10,983,067 B2 * | 4/2021 | Lindner ................ G01N 21/94 |
| 2005/0011263 A1 | 1/2005 | Harris |
| 2006/0000281 A1 * | 1/2006 | Harris .................... G01N 33/46 73/579 |
| 2009/0188320 A1 | 7/2009 | Greenough et al. |
| 2013/0003925 A1 * | 1/2013 | Oden ..................... G01N 33/46 378/58 |
| 2014/0202250 A1 * | 7/2014 | Murakoshi ........... G01N 29/223 73/632 |
| 2016/0299106 A1 * | 10/2016 | Khajeh ................ G01N 29/262 |

OTHER PUBLICATIONS

Wang, et al. ; Firmness Evaluation by Drop Impact Characteristics for Peach ; International Journal of Food Properties, 9:3 ; pp. 439-451 ; Feb. 6, 2007 ; 15 Pages.

Steiger, et al. ; Non destructive evaluation of elastic material properties of cross-laminated timber (CLT) ; Conference COST E53 ; Oct. 29-30, 2008 ; 12 Pages.

Hu ; Local Variation in Bending Stiffness in Structural Timber of Norway Spruce ; Oct. 10, 2014 ; 83 Pages.

Brashaw, et al. ; Nondestructive Testing and Evaluation of Woof: A Worldwide Research Update ; Forest Products Journal, vol. 59, No. 3 ; Mar. 2009 ; 8 Pages.

Sriskantharajah, et al. ; Review of In-service Assessment of Timber Poles ; 11 Pages.

Martins, et al. ; Review of In-service Assessment of Timber Poles ; BioResources 12(2) ; pp. 2269-2283 ; 2017 ; 15 Pages.

Hron, et al. ; Nondestructive Strength Assessment of In-Place Wood Utility Poles ; Journal of Performance of Constructed Facilities 25(2) ; pp. 121-129 ; Mar./Apr. 2011 ; 9 Pages.

\* cited by examiner

APPARATUS AND METHOD FOR GENERATING, MEASURING, AND EVALUATING VIBRATIONAL MODES IN CYLINDRICAL OBJECTS

BACKGROUND

Field of the Disclosure

The present disclosure relates to the evaluation of structural integrity of cylindrical objects by non-destructive methods.

Description of the Related Art

The building sector is in a steady quest for methods that help in the assessment of the integrity of construction elements. To this end, the lumber industry relies on the availability of high quality wood cut from hewn trees. Lumber may then be sawn from logs cut on the tree trunk. Prior to felling a tree, however, knowledge of the health status of the tree is necessary in order to ensure, with considerations to ecological integrity, the wood processing operation is efficient. Several methods and techniques have been proposed for evaluating the structural integrity of cylindrical objects such as a trunk of a tree, these methods and techniques often requiring the use of special equipment dedicated solely to the assessment of wood quality. Certain of these techniques employ acoustics in order to excite the wood so that a subsequent response, indicative of the quality of the wood, may be measured and evaluated. Other techniques employ electrical voltage applied between two nearby positions on the wood to determine an electrical resistance measured therebetween indicating soundness of the wood. Other more elaborate techniques, such as those using penetrating X-rays or gamma rays, have been proposed as methods of investigating an interior of the wood.

Generally, however, the above-described methods can only be used to identify specimen defects when at an advanced stage. This can include, for instance, the identification of rotted wood or stressed concrete at stages sufficiently advanced such that a majority of the material has already been removed. As the ability to identify a defect increases with the advanced stage of the defect, the reliability of such methods decreases as the presence of corrosion, delamination, and decay often corresponds to increased moisture levels that can obfuscate results.

Therefore, the present disclosure describes a robust method for evaluating wood quality.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a method, apparatus, and non-transitory computer-readable storage medium for evaluation of structural integrity of cylindrical objects.

According to an exemplary embodiment, the present disclosure further relates to a method for determining a structural quality of a cylindrical element, comprising measuring, by processing circuitry and as a result of a single applied force, surface vibrations of the cylindrical element via four or more surface transducers arranged on the cylindrical element along a circumference of the cylindrical element, the four or more surface transducers being equally spaced along the circumference of the cylindrical element, processing, by the processing circuitry, digital signals corresponding to each of the four or more surface transducers in order to generate a composite digital signal, transforming, by the processing circuitry, the composite digital signal to a frequency domain, comparing, by the processing circuitry, the transformed composite digital signal to a reference composite digital signal, and determining, by the processing circuitry and based on the comparing, the structural quality of the cylindrical element.

According to an exemplary embodiment, the present disclosure further relates to an apparatus for determining a structural quality of a cylindrical element, comprising processing circuitry configured to measure, as a result of a single applied force, surface vibrations of the cylindrical element via four or more surface transducers arranged on the cylindrical element along a circumference of the cylindrical element, the four or more surface transducers being equally spaced along the circumference of the cylindrical element, process digital signals corresponding to each of the four or more surface transducers in order to generate a composite digital signal, transform the composite digital signal to a frequency domain, compare the transformed composite digital signal to a reference composite digital signal, and determine, based on the comparing, the structural quality of the cylindrical element.

According to an embodiment, the present disclosure further relates to a non-transitory computer-readable storage medium storing computer-readable instructions that, when executed by a computer, cause the computer to perform a method for determining a structural quality of a cylindrical element, comprising measuring, as a result of a single applied force, surface vibrations of the cylindrical element via four or more surface transducers arranged on the cylindrical element along a circumference of the cylindrical element, the four or more surface transducers being equally spaced along the circumference of the cylindrical element, processing digital signals corresponding to each of the four or more surface transducers in order to generate a composite digital signal, transforming the composite digital signal to a frequency domain, comparing the transformed composite digital signal to a reference composite digital signal, and determining, based on the comparing, the structural quality of the cylindrical element.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
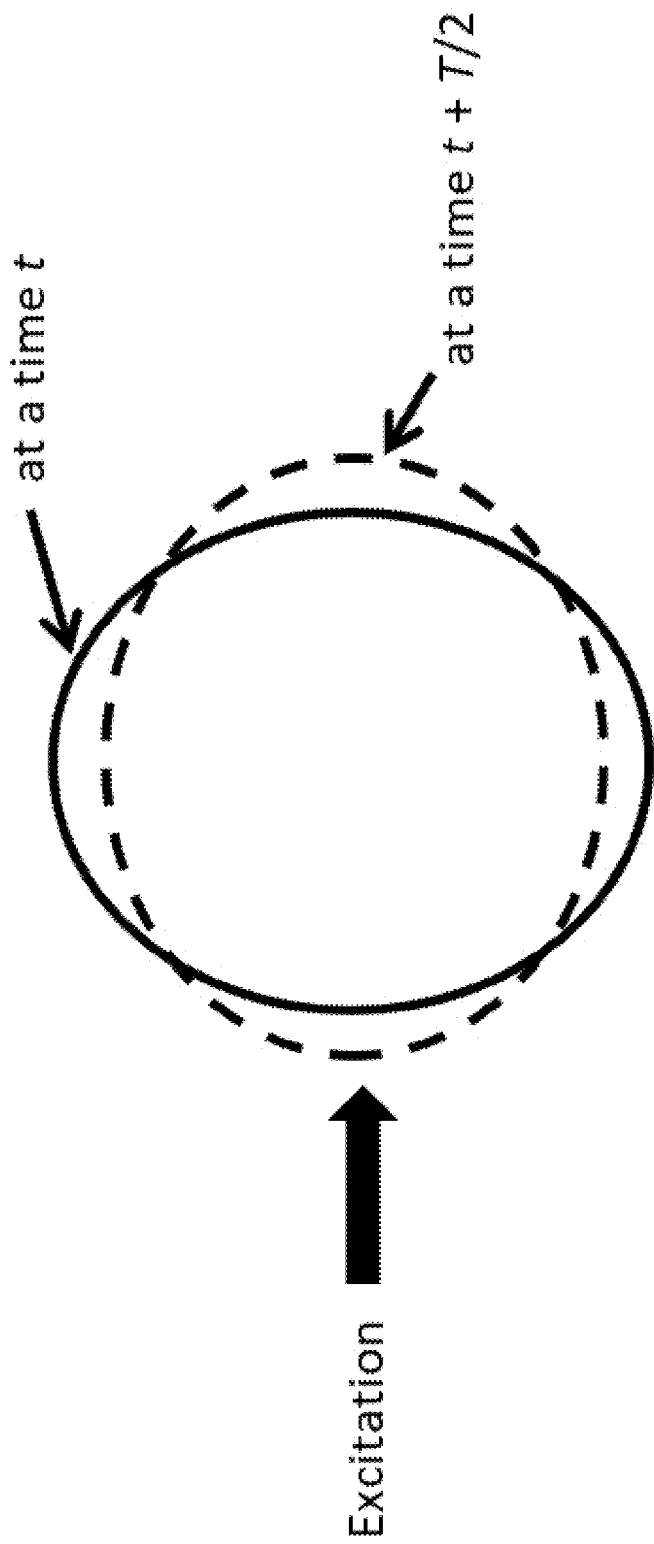
FIG. 1 is an illustration of an ovaling mode for a cylinder when radially excited, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

According to an embodiment, the present disclosure describes a method for exciting and tracking certain types of extensional modes of vibration in a cylindrical element of material. These extensional modes of vibration include those that do not appreciably-depend on axial extension, instead impacting only a cross-section of the material. For instance, the extensional mode may be an ovaling mode of vibration. The material may be hollow or solid.

In an embodiment, the method of the present disclosure includes exciting natural vibrational modes of a cylindrical element in a low band of frequencies. The natural vibrational modes include extensional modes such as ovaling mode.

Ovaling deformations of a structure are defined as a deformation of the cross section of this structure without bending deformation in the longitudinal axis of symmetry. The ovaling mode is the second order resonant frequency (e.g. $2^{nd}$ order harmonics) in the extensional, or axial, direction. The second order resonant frequency is typically less than 2000 Hz. This mode of vibration is characterized by the fact that the cross-section of the cylindrical element is deformed under the effect of the excitation while the axis of the cylindrical element, though it can move under vibration, remains the axis of symmetry. In other words, the cylindrical element under test endures shaking but not bending. Moreover, as the ovaling mode is an extensional mode of vibration in cylindrical elements, its action is restricted to the cross-section of the element and is therefore affected to a very low degree, or not at all, by the length of the element in the axial direction.

As is relevant to the present disclosure, the ovaling mode for a cylindrical element is related to its structural integrity. A shift in the magnitude of the resonant frequencies toward lower values indicates a structural fault such as deterioration due to wood attacking insects, fungi in wood, stress cracks in concrete, corrosion in steel, inhomogeneities in polymer matrices, and the like. The relative shift in the magnitude of the resonant frequency of the ovaling mode is directly related to the extent of strength degradation due to a fault in the cylindrical element. Moreover, an amplitude of the ovaling mode correlates to a size of a fault of the cylindrical element.

The resonant frequency of the ovaling mode of a specimen under test can be determined by measurement of its surface vibrations with at least one vibration sensor attached to the specimen. At least one sharp spike holding a vibration sensor, or signal transducer, may be fixed or screwed near the base of the specimen, or in a region of concern. In a non-limiting example, the vibration sensor may be a piezo-electric transducer.

In order to differentiate between the various vibration modes of the specimen under test, and more specifically to enhance and isolate the ovaling mode from the overall frequency response, one or more vibration inducers may be attached at diametrically opposed positions on the surface of the specimen under test. The vibration requirement for the ovaling mode is that the two diametrically opposite vibrations induced are in phase, meaning that they are simultaneously at a maximum of vibration or at a minimum vibration at an odd number of half periods later. In an embodiment, the one or more vibration inducers may be two synchronous vibration inducers in order to distribute the vibrations more evenly around the axis of the cylindrical structure.

In an example, the synchronicity of the vibrations causes superposition of equal but opposite waves of equal amplitude and frequency, yielding a standing wave of twice the amplitude of either of the generated waves. For a standing wave, the harmonics can be identified as n=1, n=2, etc., where n=2 is the ovaling mode. In the field, a pair of similar and synchronized hammers, or equivalent devices, may be used to generate simultaneous strikes. However, it can be appreciated that only one vibration inducer is required in order to generate the required harmonics.

According to an embodiment of the present disclosure, sensing of ovaling mode as the vibrational mode is accomplished through processing data signals from signal transducers at four or more different positions on a cylindrical element. During implementation, excitation of vibrations in the cylindrical element may be generated by a signal generator so as to be repeatable at each of the four or more positions on the cylindrical element, if required. The data signals measured at each of the four or more positions may be recorded for post-processing of the vibratory response, or impulse response, of the specimen under test.

According to an embodiment, the four or more measurement positions are on a same circumference on a specimen under test, which can be cylindrical element. The four or more measurement positions may be antinodes of the ovaling mode (i.e. one position directly above (or below) a single force application of the excitatory force and the other diametrically opposed), the corresponding signal transducers being positioned equidistant from each other. Therefore, vibrations of the ovaling mode are in phase at two diametrically opposed positions on the cylindrical element. In this way, as will be described with reference to FIG. 3, each pair of diametrically opposed signal transducers are in opposite phase from the other, such that an amplitude of vibration is maximal for one pair while an amplitude of vibration is minimal for the other pair. In other words, the cylindrical element is deformed to its maximum extension for one pair while the other pair is deformed to its maximum contraction, and vice versa.

According to an embodiment, and as will be described with respect to FIG. 5, the use of four or more signal transducers allows for monitoring of the ovaling mode of the cylindrical element to be enhanced through the combination of the in-phase response and out-of-phase response. For instance, data signals from each of the signal transducers of a diametrically opposed pair may be combined to form an additive pair signal, one additive pair signal then being subtracted from the other additive pair signal in order to 'amplify' the response of the cylindrical element and form a composite signal.

According to an embodiment, the composite signal, which may be digitized, may then be transformed into a frequency domain by, among others, Fourier transform. The transformed composite signal may then be analyzed in order to determine frequencies of modes of interest. For instance, the ovaling mode may be isolated and a resonant frequency of the ovaling mode of the cylindrical element may be compared to that of a reference cylindrical element of known qualities, including cross-sectional size. The stiffness of the material of the cylindrical element and the degree of its soundness may be determined by this comparison.

According to an embodiment, the above-briefly described method may also be used for cross-sectional vibrational modes of an order higher than that of ovaling. In these cases, and in comparison with a thin cylindrical shell, the circumference of the cylindrical element would correspond to an even multiple of bending wavelengths.

According to an embodiment, the present disclosure demonstrates and relies upon the dependency of resonant frequency (e.g. <2000 Hz) of the cross-sectional mode of second order in a cylindrical element, or ovaling mode, on the structural integrity of a specimen under test. The specimen under test may be a concrete column, a pole, a log, or similar test specimen. A predictable shift in the magnitude of these resonant frequencies towards lower values occurs as the condition of the specimen under test is deteriorated due to external agents, including corrosion of reinforced concrete columns or deterioration of wooden poles, wooden logs, and standing trees by fungi and insects. As indicated previously, the relative shift in the magnitude of the resonant frequencies of the ovaling mode is directly related to the extent of strength-weakening attack.

As introduced previously, the resonant frequency of the ovaling mode of the specimen under test can be determined through a measurement of its surface vibrations by means of a vibration sensor attached thereto. In the laboratory, the presence of the ovaling mode in the frequency response curve is achieved through vibration of the specimen under test via an electro-dynamic shaker. In the field, however, this may be done through a strike from a hammer or equivalent device. Moreover, when applied at each of four or more measurement positions on the cylindrical test specimen, the ability to provide the same excitation signal at each position allows for enhancement of the presence of the ovaling mode. The measurement positions may be chosen at successive 90 degrees displacements on the same perimeter of the cylindrical test specimen. As described, analog signals collected by each vibration sensor may then be transmitted to processing circuitry to be digitized for processing and analysis. The processing comprises submitting the digitized signal to an operation where, first, the signals from two opposite positions (signals in phase) are summed resulting in two signal pairs, and second, the two signal pairs are subtracted from each other (signals in anti-phase). The final result of these operations is a signal that will be submitted to a discrete fast Fourier transform (FFT), from which the amplitude and resonant frequencies may be determined. Alternatively, the analog vibration signals can be stored on a tape or on a digital medium (e.g., MP3, way) to be replayed for processing and analysis at a later time.

According to an embodiment, the present disclosure describes an accurate, effective, and inexpensive method for inspecting the strength of a cylindrical element. This can encompass, but is not limited to, construction columns and pillars made of steel, wood or concrete, wooden poles, logs, and trunks of standing trees. The method includes analysis and generation of a final assessment on the health status of the specimen under test. In an embodiment, the above method may be performed on a portable apparatus comprising a laptop computer and the hardware/software to be used for the digital conversion and analysis of the analog signals recorded from the specimen under test. The application of the present disclosure can be implemented on hollow or solid cylindrical specimens.

It is an objective of the present disclosure to provide a structural resonant frequency testing method that is simple to perform, fast, accurate and inexpensive.

Further, it is an objective of the present disclosure to provide for evaluation of material fatigue and detection of defects, either structural or resulting from strength weakening processes acting within the material.

According to an embodiment, the present disclosure describes a method of determining the condition of a cylindrical element of solid material, the cylindrical element being, among others, a concrete column, a pillar, a tree trunk, a log, or a wooden pole. The cylindrical element may be filled (i.e., solid) or hollow (i.e., shell). In an embodiment, the method comprises initiating the natural vibrations of the cylindrical solid material element in the radial direction and in a frequency range that covers the lowest three natural modes of vibration of a cross-sectional nature. Excitation of the test cylindrical element may be accomplished through the action of a vibration exciter attached to the body of the cylinder or, alternatively, through a stroke with a hammer. The response of the cylindrical element may be recorded by means of a signal transducer generating an electrical voltage equivalent to the vibrational motion of the cylindrical element, including cross-sectional modes thereof. In an embodiment, the same excitation signal may be applied at four well-specified positions on the circumference of the cylindrical element, the resulting vibratory response being sensed by the signal transducer, or vibration sensor. In another embodiment, the excitation signal may a single excitation signal. The four voltage electrical responses of the signal transducers may be converted to digital signals and sorted into signal pairs, wherein each pair includes the digital signals associated with two diametrically opposed positions. The signals at two diametrically opposed positions may be added in order to obtain two signal sums, a difference therebetween then being determined to obtain a signal difference. A digital FFT may be executed on the signal difference for acquiring the Transfer Function, or frequency response, of the even cross-sectional vibration modes, including the ovaling mode. The frequency of the second natural even cross-sectional vibration mode of vibration (i.e., the ovaling mode) of the cylindrical element may be determined from a graph of the amplitude of the transfer function. Based on charts pre-established for the resonant frequencies of the ovaling mode as a function of the cross-sectional size of intact cylindrical elements, a comparison can be made between the value of the measured frequency and the corresponding intact frequency on the chart for evaluating the soundness of the inspected cylindrical element. Accordingly, a reading of the resonant frequency of the ovaling mode permits the evaluation of the stiffness of the cylindrical wood element and assessment of its soundness status by way of color classification, wherein the color classification is assigned in order of material soundness.

According to an embodiment, the resonant frequency of the ovaling mode of a specimen can be determined by measurement of its surface vibrations with at least one vibration sensor attached to the specimen. At least one sharp spike holding a vibration sensor may be fixed or screwed near the base of the specimen, or in a region of concern. In a non-limiting example, the vibration sensor may be a piezoelectric transducer. In a non-limiting example, the piezoelectric transducers for tree measurements may be a 4371 piezoelectric force transducer manufactured by Brüel & Kjær. (See "Type 4371-Bruel &Kjaer Sound and Vibration", Bruel & Kjaer North America Inc. (HQ), 3079 Premiere Parkway, Suite 120, Duluth, Ga. 30097, U.S.A.) and configured to measure vibrations in the frequency range of 1 to 2000 Hz. An electrical voltage response equivalent to the vibratory motion of the structure acquired through the at least one sensor. The electrical response is converted to a digital signal and then transformed into the frequency domain for determining the frequencies of the modes of interest. The resonant frequency of the (waling mode of the element is then compared to that of a sound element with comparable cross-sectional size to establish the stiffness and soundness degree of the cylindrical element.

According to an embodiment, the color classification may be green for sound materials, yellow for acceptable materials, orange for materials requiring caution, and red for materials that should be rejected.

According to an embodiment, consideration is made to green wood in standing trees or in logs of freshly hewn trees. For wooden poles or cylindrical elements of solid materials other than wood (e.g., columns or pillars of reinforced concrete), corrosion or host manufacturing defects can impact the soundness of the cylindrical element. For such materials, other reference charts can be established.

In an embodiment, for a non-perfectly cylindrical specimen, such as a wooden pole or a tree trunk, the response of the ovaling mode on the frequency scale m depend on the taper, or change in geometrical shape along the axis of the element. For a wooden pole, which can be modelled as a beam clamped at one of its ends attachment at the ground level), a further consideration is the general condition of the portion of the structure above the ground. In accordance with the present disclosure, the wood species must be a factor in the mathematical model. Similarly, for concrete, polymer or steel constructions, the concrete, polymer and steel compositions must be factors in the model.

According to an embodiment, the vibration exciter can apply natural cross-sectional vibrations of the cylindrical element in the frequency range between 0 and 2000 Hz. This can be achieved by controlling the nature of the contacting areas used for generating the stress pulse in the specimen under test.

According to an embodiment, the present disclosure describes a method for determining the stiffness of a cylindrical element, comprising initiating the natural vibration of the cylindrical element in a frequency band that covers at least two of the first cross-sectional resonant modes of vibration, generating an electrical response equivalent to the surface vibrational motion of the body, determining the frequency of the ovaling mode of vibration according to the cross-sectional size of the cylindrical element and the solid material it is made of, formulating a mathematical model of the element, from which the natural frequencies of the ovaling mode of vibration model may be modeled and drawn on a graph expressing the resonant frequency as function of cross-sectional size (e.g., average circumference, average diameter), comparing the value of the measured resonant frequency of the ovaling mode on the inspected cylindrical element with the value read on the graph for the corresponding cross-sectional size of the sound cylindrical element, and determining the degree of soundness of the tested cylindrical element therefrom. In an embodiment, three "soundness" regions can be established. These "soundness" regions can include a "green" region when the strength of the cylindrical element is above 85% of the reference sound cylindrical element of corresponding size, a "yellow" region when the strength of the cylindrical element is below 85% but above 70%, an "orange" region when the strength of the cylindrical element is below 70% but above 55%, and a "red" region when the strength of the cylindrical element is less than 55%. It can be appreciated that, for wood elements, the strength of the element depends to a high degree on the extent of its affliction by rot. Similarly, for steel, it may be rust, and for concrete it may be corrosion. Moreover the change of material strength is not due only to the change of the material properties at the microscopic level but to the presence of strength-weakening defects (e.g., knots and cross-grain for wood, voids, delamination and external agents in concrete and steel) as well as a poor processing of the material or defective operation during its manufacturing (e.g. casting, filling, tempering, cooling). Such defects may be estimated from the change in the value of the frequency of the ovaling mode.

Figure 2:
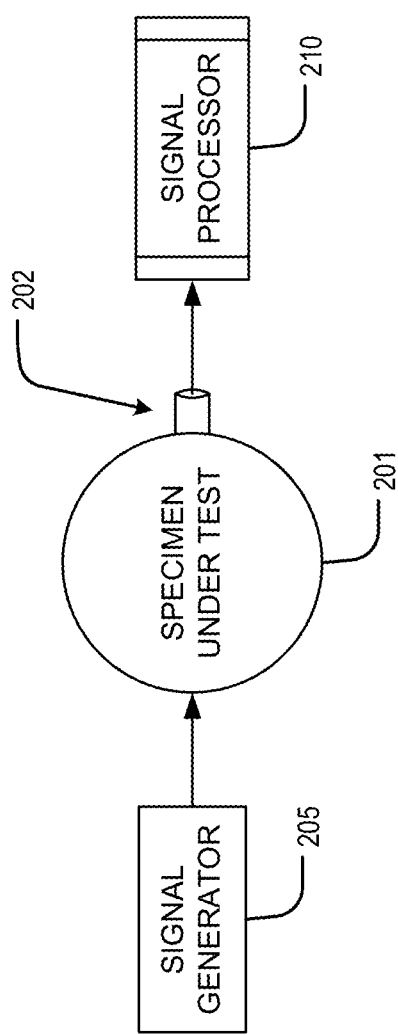
FIG. 2 is a high-level flow diagram of a method for generating, measuring, and evaluating vibrational modes in cylindrical bodies, according to an exemplary embodiment of the present disclosure.

Turning now to the Figures, and in view of the above description of the present disclosure, FIG. 1 is an illustration of an ovaling mode set into vibration through a radial excitation by a single force in a solid cylindrical element. The solid line indicates a shape of a circumference or perimeter of the solid cylindrical element at time t, reflecting a minimum amplitude response in a given direction. The dashed line indicates a shape of the circumference or perimeter of the solid cylindrical element at time t+T/2, reflecting a maximum amplitude response in the given direction, wherein T is 1/f and f is the resonant frequency of the ovaling mode. In order to evaluate the system introduced in FIG. 1, the high-level schematic of FIG. 2 may be employed according to the descriptions herein. A signal generator 205 may be used for applying an excitatory stimulus to a specimen under test 201. In a non-limiting example, the signal generator 205 may be a Keysight Technologies 33210A Signal Generator, available from allied Electronics and Automation, Allied Electronics, Inc., 7151 Jack Newell Blvd. S., Fort Worth, Tex. 76118 U.S.A. and may be configured to apply an excitatory stimulus over a frequency range between 10 and 15 kHz. For the purposes of measurement, the specimen under test 201 may be considered to be mounted (or grown, in the case of a tree) upon a ground plane with its axial length perpendicular to the surface. Resultant vibrations generated within the specimen under test 201 may be measured by at least one signal transducer 202. The at least one signal transducer 202 may be attached by a spike, in the case of a wooden test element, or by epoxy, in the case of a concrete or steel test element Alternatively, the at least one signal transducer 202 may be attached by bolts inserted into holes drilled in the test surface, although this method may not be feasible in some instances, as it may be destructive to the structural integrity or the esthetics of the cylindrical test object. Signals generated at the at least one signal transducer 202 can be transmitted to a signal processor 210 in order to be prepared for analysis and a determination as to the soundness of the specimen under test 201.

Figure 3:
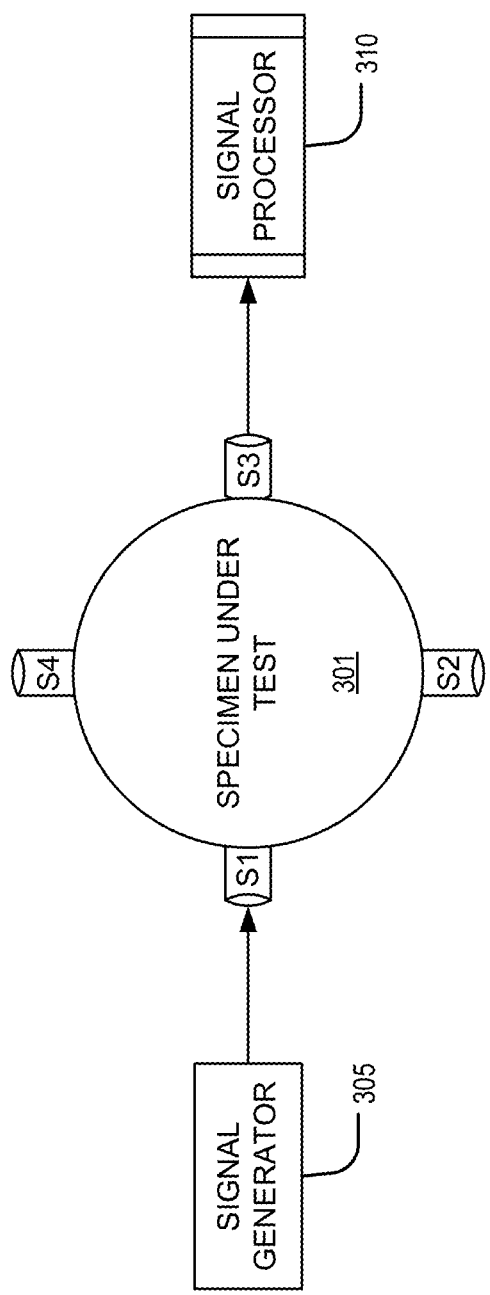
FIG. 3 is a high-level flow diagram of a method for generating, measuring, and evaluating vibrational modes in cylindrical bodies, according to an exemplary embodiment of the present disclosure.

FIG. 3 is an exemplary schematic of a system of the present disclosure, wherein the at least one signal transducer is four or more signal transducers S1, S2, S3, S4. Similar, a signal generator 305 can be configured to apply an excitatory stimulus to a specimen under test 201. Resultant vibrations generated within the specimen under test 201 may be measured by each of the four or more signal transducers S1, S2, S3, S4. The four or more signal transducers S1, S2, S3, S4 may be arranged at 90° spacing from a center of the specimen under test 301, or equidistant from each other. The excitatory stimulus can be applied immediately above or below one of the four or more signal transducers S1, S2, S3, S4 in order to enhance the measured ovaling mode response of the specimen under test 301. As introduced above and in context of FIG. 1, the arrangement of the signal transducers allows for paired, diametrically opposed signal transducers to be reconciled in order to enhance the ovaling mode response. Outputs of the paired, diametrically opposed signal transducers can then be factored together to arrive at a further enhanced composite signal that exploits the ovaling mode of the specimen under test 301. Such processing of signals from the four or more signal transducers S1, S2, S3, S4 can be performed by a signal processor 310. The signal processor 310, as described in FIG. 4, can be further configured to evaluate the specimen under test 301 and determine its soundness or structural quality.

According to an embodiment, and in a non-limiting example of the present disclosure, the signal generator 305 of FIG. 3 may be employed to initiate a transient vibration in the specimen under test 301. The specimen under test 301 may be a construction column, a bridge pillar, a log, a wooden pole, a tree trunk, and the like, or another cylindrically shaped element that may be solid, hollow, or filled. For a construction column, a wooden pole in service, or a standing tree, the signal generator 305 may apply an excitatory stimulus to the specimen under test 301 at a height of approximately three to four feet above ground level, the excitatory stimulus initiating the transient vibration. In an instance, a force-generating transducer firmly attached to the specimen under test 301 can be used in order to generate a time-extended excitatory stimulus. In another instance, the excitatory stimulus may be generated by a hammer stroke on the specimen under test 301, the hammer stroke being transitory and in the form of a mechanical stress. The four or more signal transducers S1, S2, S3, S4 may be positioned around a circumference of the specimen under test 301 such that one of the four or more signal transducers S1, S2, S3, S4 is directly above or below the position of the applied excitatory stimulus. Each of the four or more signal transducers S1, S2, S3, S4 may be arranged such that at least one signal generator 305 applies an excitatory stimulus proximate a corresponding one of the four or more signal transducers S1, S2, S3, S4. For instance, a height of each of the four or more signal transducers S1, S2, S3, S4 may be between 3 inches and 10 inches below a height of an applied excitatory stimulus.

The one of the four or more signal transducers S1, S2, S3, S4 proximate the applied excitatory stimulus is arranged out of a local area of the applied excitatory stimulus that may be impacted by local deformations, thereby minimizing its blurring effects on the ovaling mode response. Each subsequent one of the four or more signal transducers S1, S2, S3, S4 positioned around the circumference of the specimen under test 301 may be arranged at 90° steps from the direction of the applied excitatory stimulus, as shown in FIG. 3. Vibrations generated within the specimen under test 301 may then be measured as a time-dependent voltage at each of the four or more signal transducers S1, S2, S3, S4.

In an embodiment, the electrical signals generated at each of the four or more signal transducers S1, S2, S3, S4 may be processed in real-time or recorded for processing at a later time. For instance, the electrical signals, or analog signals, generated in response to vibrations within the specimen under test 301 may be conveyed to a signal recorder for later processing. In another instance, the analog signals generated in response to vibrations within the specimen under test 301 may be immediately processed by the signal processor 310. The signal processor 310 may perform a method as described in subsequent Figures, including digitization of the analog signals, mathematical operations on the resultant digital signals associated with each signal transducer, and analysis of a final composite digital signal to evaluate the specimen under test 301. The method may include amplification of the analog signals, as appropriate. The analysis may include execution of a FFT to transform the composite digital signal to the frequency domain, resulting in a transfer function. The graphed transfer function may then be analyzed to determine a resonant frequency and amplitude associated with the ovaling mode. Subsequently, a stiffness of the specimen under test 301 may be determined depending on a type of the specimen under test 301 and a cross-sectional size (e.g. perimeter, average diameter) of the specimen under test 301.

Figure 4:
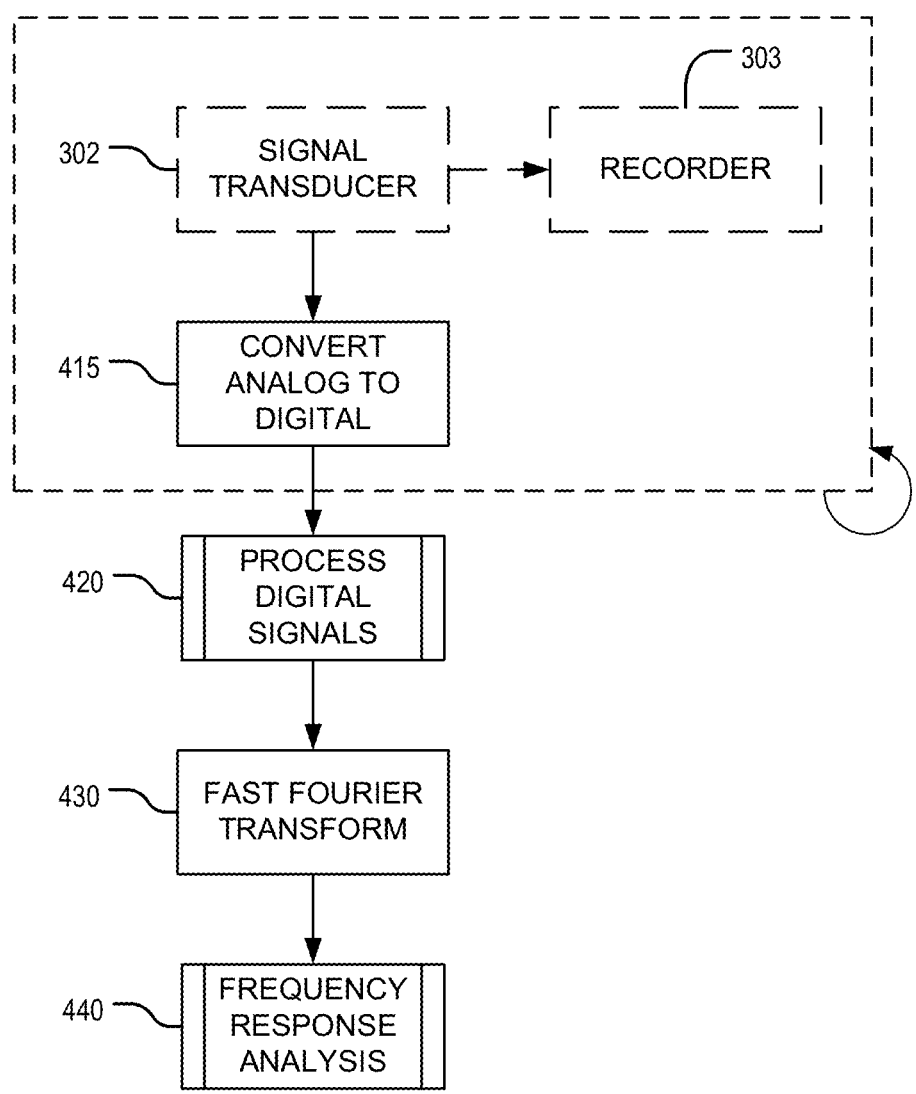
FIG. 4 is a low-level flow diagram of a method for evaluating vibrational modes in cylindrical bodies, according to an exemplary embodiment of the present disclosure.

The signal processing 310 introduced above will now be described in greater detail with reference to the signal processing method 410 of FIG. 4.

According to an embodiment, an analog signal measured at a signal transducer at step 302 may be conveyed to a recorder at step 303 for processing at a later time. In a non-limiting example, the analog signal measured at each signal transducer may at step 302 may be recorded by a signal recorder such as a Paperless Recorder/Data Acquisition System, Item #RD8800-C24, available from Omega Engineering, 800 Connecticut Ave. Suite 5N0 Norwalk, Conn. 06854 USA. Alternatively, or in addition to step 303, the analog signal measured at the signal transducer at step 302 may be directly processed according to method 410. Method 410 includes, initially, conversion, at step 415, of the analog signal measured at the signal transducer to a digital signal that is able to be processed by a computer system. In view of FIG. 3, it can be appreciated that the analog signal measured at the signal transducer may be one of a plurality of analog signals measured at a plurality of signal transducers, wherein the 270° arrow indicates such recording and/or analog-to-digital conversion may be iterative, as needed.

In a non-limiting example of the present disclosure, the plurality of signal transducers is four signal transducers, as shown in FIG. 3. The four signal transducers may be, among others, piezoelectric transducers, as described above.

At sub process 420 of method 410, the digitized signals from the four signal transducers may be processed. Processing the digital signals allows for double enhancement of the ovaling mode of the specimen under test. As shown in FIG. 5, sub process 420 includes a processing flow diagram for generating a composite digital signal from digital signals associated with each of four signal transducers S1, S2, S3, S4.

Initially, the analog signals from each of the four signal transducers S1, S2, S3, S4 may be converted to digital signals by an analog-to-digital converter 515. Digital signals associated with diametrically opposed signal transducers may then be added together to generate a summed digital signal. To this end, and in view of the exemplary signal transducer arrangement of FIG. 3, digital signal D1 521, associated with signal transducer S1, may be added together with digital signal D3 523, which is associated with signal transducer S3, to generate digital signal E1 525. Similarly, digital signal D2 522, associated with signal transducer S2, may be added together with digital signal D4 524, which is associated with signal transducer S4, in order to generate digital signal E2 526. Such addition generates a first form of enhancement of the ovaling mode. For instance, assuming an excitatory stimulus is applied in the direction of signal transducer S1, the digital signals associated with signal transducer S1 and signal transducer S3 will, in ovaling mode, reflect a maximum amplitude signal at time t while the digital signals associated with signal transducer S2 and signal transducer S4 will, in ovaling mode, reflect a minimum amplitude signal at time t. The addition of these signals, therefore, reflects a first enhancement. A second enhancements comes when the difference of digital signal E1 525 and digital signal E2 526 is determined in generate a composite digital signal F1 527. By subtracting the minimum amplitude signal from the maximum amplitude signal, composite digital signal F1 527 reflects a second enhancement of the ovaling mode of the specimen under test.

Figure 5:
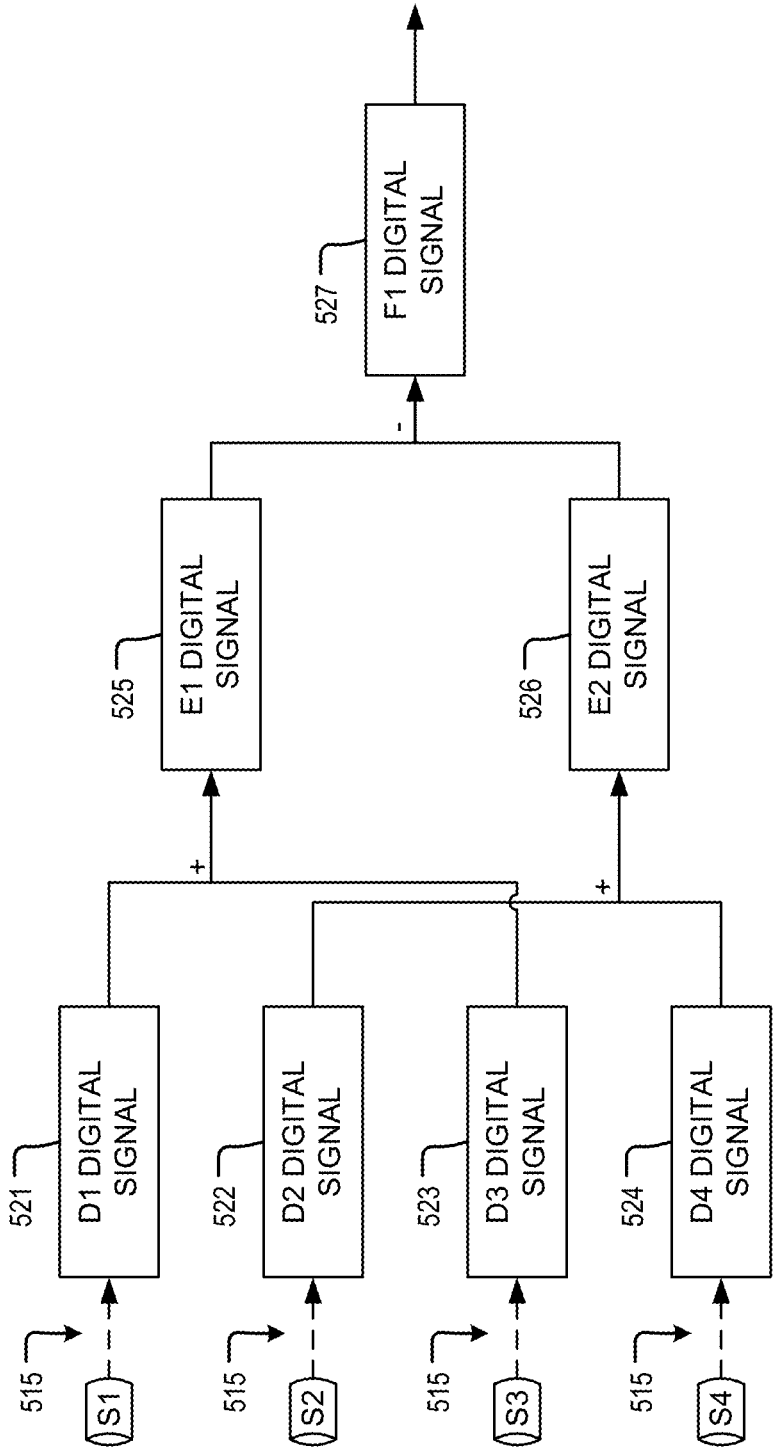
FIG. 5 is a flow-diagram of a sub process of a method for evaluating vibrational modes in cylindrical bodies, according to an exemplary embodiment of the present disclosure.

Returning now to FIG. 4, the composite digital signal F1 527, or simply the composite digital signal, of FIG. 5, may be transformed in to the frequency domain at step 430 of method 410. The transformation may occur by FFT, in an example, or by other method of transforming time-dependent voltage data into a frequency domain.

The transformed composite signal may be then be submitted to a frequency response analysis at sub process 440 of method 410. Sub process 440 of method 410 may include determination of a structural quality of the specimen under test and/or a defect type of the specimen under test, as is described in greater detail with reference to FIG. 6.

The above-described method 410 will now be described as implemented within an experimental test of a specimen under test. The specimen under test may be a cylindrical element. To perform the experimental test, an operator may record a type of the specimen under test and a diameter, or other cross sectional indicator, of the specimen under test. The operator may then initiate vibrations within the specimen under test by means of an excitatory stimulus provided by, in an example, a hammer of appropriate size and suitable tip hardness in order to excite the ovaling mode of vibration. The hammer impact may be at any location on the specimen under test but is preferably to be at about three to four feet up from the ground-line. The stroke of the hammer is to be directed in a radial direction on the surface of the specimen under test.

Four signal transducers may be firmly attached on the surface of the specimen under test at equidistant positions on the same circumference. One of the four signal transducers may be positioned directly above a position of the excitatory stimulus. Accordingly, the four signal transducers are arranged in order to optimally capture the ovaling mode response of the specimen under test, referred to as troughs or anti-node positions of the vibration mode. Analog signals generated at each of the four signal transducers may be recorded if later analysis is desired. Alternatively, the analog signals from each of the four signal transducers can be processed and analyzed in real-time. To this end, each analog signal can be converted into a digital signal by an analog-to-digital converter. Each digital signal may then be processed together to generate a composite signal reflecting an ovaling mode response of the specimen under test. In an embodiment, a FFT may be applied to the composite signal. In another embodiment, an FT may be applied to the composite signal.

In a non-limiting example, and as described in U.S. patent application Ser. No. 16/401,212, which is incorporated herein by reference in its entirety, a frequency response of a system may be characterized by a characteristic transfer function $H(\omega)$. When input $f(t)$ is applied to the system as a function of time t, the system responds with output $g(t)$, satisfying below relation.

$$G(\omega) = H(\omega)F(\omega), \quad (1)$$

where $F(\omega)$ and $G(\omega)$ are Fourier Transformations (FT) of input $f(t)$, and output $g(t)$, respectively. Thus, a response or output $g(t)$ of the system against the input $f(t)$ is given by the Inverse Fourier Transformation (IFT) of $G(\omega)$, $$g(t) = \frac{1}{2\pi} \int_{\infty}^{\infty} H(\omega)F(\omega)\exp(j\omega t)d\omega. \quad (2)$$

Now, assuming the input function $f(t)$ is a unit impulse represented by the delta function $\delta(t)$, and the output against the delta function input is given by $h(t)$, then, the FT of the input is given by $$F(\omega) = \int_{\infty}^{\infty} \delta(t)\exp(-j\omega t)dt = 1. \quad (3)$$

Therefore, $$G(\omega) = H(\omega)F(\omega) = H(\omega) = \int_{\infty}^{\infty} h(t)\exp(-j\omega t)dt. \quad (4)$$

Eq. (4) means $G(\omega)$, namely the FT of the output function $h(t)$ gives the characteristic transfer function $H(\omega)$ of the system when the input $f(t)$ is the delta function or a short impulse which can approximate the delta function.

On the other hand, when the input function $f(t)$ is too broad to approximate the delta function, the response $g(t)$ is given by below convolution taking time delay $\tau$ of responses into account, $$g(t) = \int_\infty^\infty h(\tau)f(t-\tau)d\tau. \quad (5)$$

Here, $h(t)$ is the impulse response output when the input is the delta function $\delta(t)$. Taking FT of above Eq. (5), $$G(\omega) = \int_\infty^\infty g(t)\exp(-j\omega t)dt = \int_\infty^\infty \left[\int_\infty^\infty h(\tau)f(t-\tau)d\tau\right]\exp(-j\omega t)dt = \quad (6)$$

$$\int_\infty^\infty h(\tau)\exp(-j\omega\tau)d\tau \int_\infty^\infty f(t-\tau)\exp[-j\omega(t-\tau)]d(t-\tau) =$$

$$H(\omega)F(\omega).$$

Therefore, $$H(\omega) = \frac{G(\omega)}{F(\omega)} \quad (7)$$

where, $$H(\omega) = \int_\infty^\infty h(\tau)\exp(-j\omega\tau)d\tau, \quad (8)$$

$$F(\omega) = \int_\infty^\infty f(t)\exp(-j\omega t). \quad (9)$$

Here $H(\omega)$ is the characteristic transfer function of the system, and corresponds to a FT of the impulse response $h(t)$, the output against an input of the delta function. $F(\omega)$ is a FT of the input function $f(t)$, $G(\omega)$ is a FT of the output function $g(t)$.

The above relations mean that the characteristic transfer function $H(\omega)$ can be obtained from Eq. (7), by obtaining $F(\omega)$, the FT of the input function $f(t)$ and $G(\omega)$, the FT of the output function $g(t)$ as a response to the input function $f(t)$, even when the input was not the delta function or did not approximate it. Recently, a Fast Fourier Transformation (FFT) is conventionally available utilizing a computer equipped with advanced semiconductor devices such as field programmable gate arrays (FPGA).

The characteristic transfer function $H(\omega)$ of the system contains information including resonance frequency characteristics of the system, one of the main concerns of the present disclosure. The algorithm used in the present disclosure that functions to read resonance peaks from the FT of the impulse response is also based on above relations.

As an alternative method, the characteristic transfer function $H(\omega)$ can be measured by tracing a frequency response of the system while applying a sinusoidal signal input with a constant power $$f(t) = A_0 \exp(j\omega_0 t) \quad (10)$$

and gradually sweeping the frequency of the sinusoidal signal in a frequency band of interest, 10 Hz to 15 KHz, for example. There, Eq. (9) gives the FT of the input $f(t)$ as $F(\omega) = 2\pi A_0 \delta(\omega - \omega_0)$, then Eq. (2) gives the output as $$g(t) = A_0 H(\omega_0) \exp(j\omega_0 t). \quad (11)$$

When, a phase shift $\phi(\omega_0)$ of the output signal is taken into account, Eq. (11) can be expressed as $$g(t) = A_0 H(\omega_0) \exp[j\phi(\omega_0)] \exp(j\omega_0 t). \quad (12)$$

Thus, using Eqs. (10) and (12), an amplitude ratio or a square root of power ratio of $g(t)$ to $f(t)$ directly gives $H(\omega_0)$, sweeping the frequency $\omega_0$ gives the characteristic transfer function $H(\omega)$, namely a frequency spectrum of an amplitude of the characteristic transfer function for a frequency band of interest. The amplitudes of the signals can be measured by using a phase sensitive detector or a lock-in amplifier. The phase shift $\phi(\omega_0)$ can also be measured by using the lock-in amplifier, in addition to the amplitude ratio. Thus, in this alternative approach, a frequency spectrum of the phase shift component of the characteristic transfer function can also be measured. Recent digital technology empowered by advanced semiconductor devices such as field programmable gate arrays (FPGA) enable extension of the lock-in amplifier to add various analysis functions including the ADC and the FFT. (See, "Principles of lock-in detection and the state of the art," Zurich Instruments, White Paper, 2016, https://www.zhinst.com/products/lock-in-amplifiers—incorporated herein by reference.) A combination of the electrodynamic shaker and the sinusoidal signal sweeper as the driver can be used in those alternative methods in providing the excitatory stimuli.

As a further alternative method, a broad band noise generator is used to generate approximately equal noises at all frequencies under concern. Eq. (3) indicates a flat noise input is equivalent to the delta function input. Therefore, a resulting output response $g(t)$ gives an equivalent to the function $h(t)$ which is an output function when input was the delta function. Then the FT of $g(t)$ gives the characteristic transfer function $H(\omega)$, as given by Eq. (4).

The transformed composite signal may be analyzed. A resonant frequency of the ovaling mode of the specimen under test may be determined and compared to a value on a reference curve for a cylindrical element comparable to the specimen under test. Concurrently, or prior to, an amplitude of the frequency response of the specimen under test reflected in the transformed composite signal may be evaluated. The cylindrical element comparable to the specimen under test may be a cylindrical element of a similar material and similar size as the specimen under test. Moreover, the cylindrical element comparable to the specimen under test, or reference element, is of known structural quality. For instance, the reference element is an element of sound structural quality or in otherwise good condition. Parameters of note, such as material and size, may include humidity, visible degradation, location, and the like. The comparison of the resonant frequency of the specimen under test with a resonant frequency of a reference cylindrical element includes a comparison of the value of the resonant frequency.

For example, a relative decrease of the value of the resonant frequency of the ovaling mode of the specimen under test compared with the reference cylindrical element provides information on stiffness of the specimen under test relative to baseline. In another example, a relative amplitude difference of 20% may indicate a weakened structure, such as insect infestation in trees or wooden poles or stress cracks in concrete, whereas a relative amplitude difference of 40% may indicate a cylindrical object which is unusable or may need replacement.

In an embodiment, the stiffness of the specimen under test relative to baseline can be scored, or represented, on a scale, wherein a green is associated with a sound material, a yellow color is associated with an acceptable material, an orange color is associated with a weak material, and a red color is associated with a material that should be discarded.

Figure 6:
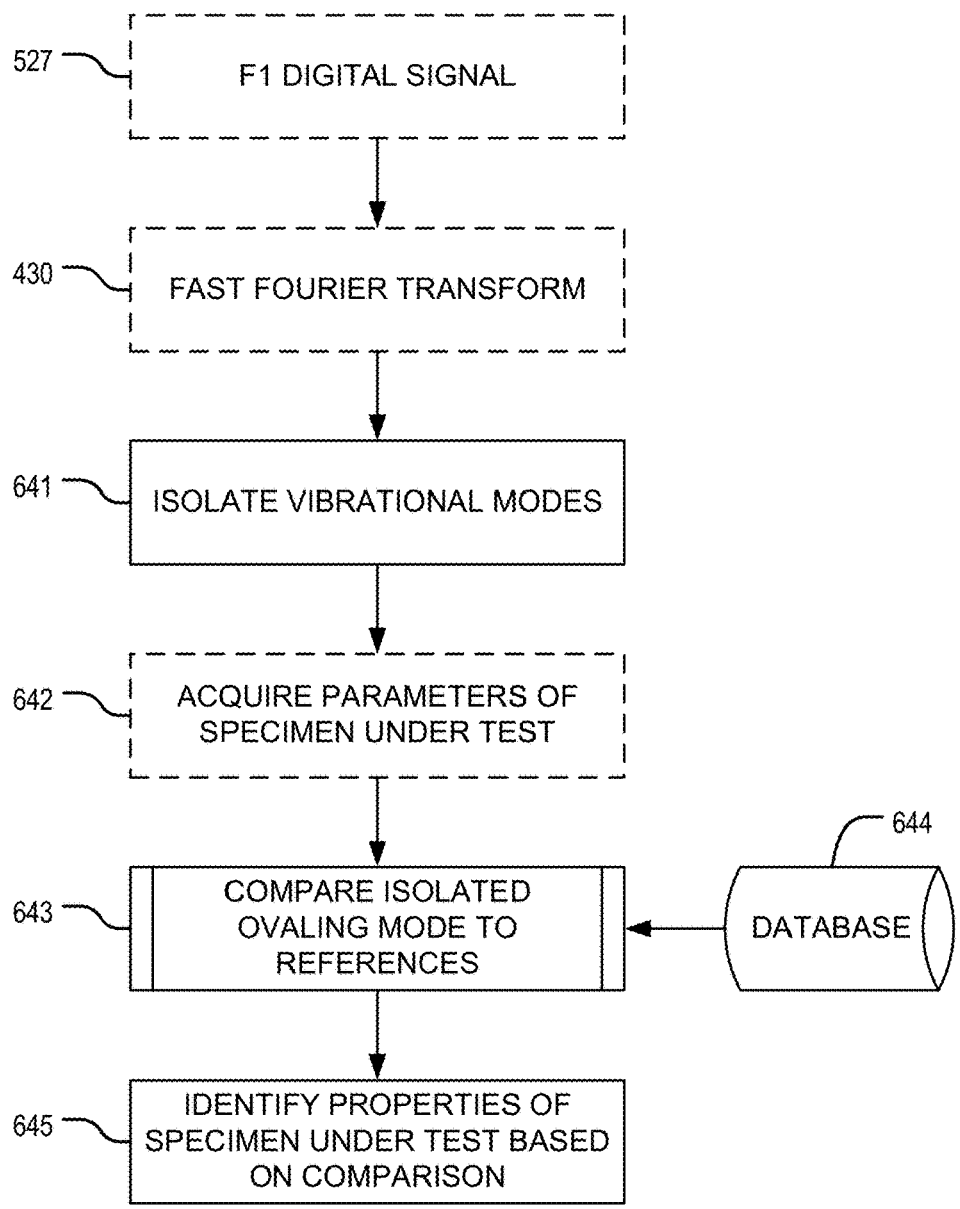
FIG. 6 is a flow diagram of a sub process of a method for evaluating vibrational modes in cylindrical bodies, according to an exemplary embodiment of the present disclosure.

Returning to the Figures, FIG. 6 is a flow diagram describing sub process 440 of method 410. As introduced previously, a composite digital signal F1 can be generated at step 527. A fast Fourier transform, for instance, may then be applied to the composite digital signal F1 at step 430 in order to generate a transformed composite digital signal, wherein the transformed composite digital signal is a representation of the vibrational response of the specimen under test in the frequency domain and can be visualized graphically.

Accordingly, at step 641 of sub process 440, an ovaling mode of the transformed composite digital signal may be isolated according to the resonant frequency of the specimen under test, wherein the resonant frequency of the specimen under test is that which generates maximum amplitude.

At step 642 of sub process 440, parameters of the specimen under test may be acquired. For instance, the type of material constituting the specimen under test, as well as the average diameter of the specimen under test, may be acquired and provided to sub process 440 for consideration during analysis, as will become apparent with reference to step 643.

At sub process 643 of sub process 440, the isolated ovaling mode of the specimen under test can be compared to a reference element obtained from a reference database 644. The reference element may be obtained from the reference database 644 according to the parameters of the specimen under test acquired at step 642 of sub process 440. In an example, the reference element may be an element similar to the specimen under test and of a known structural quality.

For instance, as described with reference to FIG. 7, if the specimen under test is a wooden pole with a diameter of one meter, the reference element obtained from the reference database 644 will necessarily be of a similar material and size and may be of sound structural quality. In another instance, as described with reference to FIG. 8, if the specimen under test is a wooden pole with a diameter of one meter, the reference element obtained from the reference database 644 will necessarily be of a similar material and size but may be of a structural quality resembling a defective material, wherein the reference element is labeled as having a specific defect.

According to an embodiment, the reference database 644 may include a corpus of materials of a variety of types, sizes, and conditions. For instance, as it relates to FIG. 7, the reference database may comprise materials of a variety types and sizes but of sound condition, wherein the resonant frequencies thereof can be used to represent a sound baseline for comparisons. In another instance, as it relates to FIG. 8, the reference database may comprise materials of a single type and size but of varying conditions, wherein the varying conditions include specific defect types and the frequency responses associated therewith be used to identify a resonant frequency and amplitude, among others. For instance, identifiable defect types of the specimen under test can include knots and cross-grain for wood, voids, delamination and external agents in concrete and steel as well as imperfections that manifest as a result of poor processing of the material or defective operation during its manufacturing, including casting, filling, tempering, and cooling.

Having obtained the reference element, a variety of comparisons may be made between the frequency response curve of the specimen under test and a frequency response curve of the reference element. Such comparison can be based on the resonant frequency and/or amplitude of the resonant frequency of the specimen under test and corresponding features of the reference element, wherein properties of the specimen under test, or structural qualities, may be determined therefrom at step 645 of sub process 440.

Figure 7:
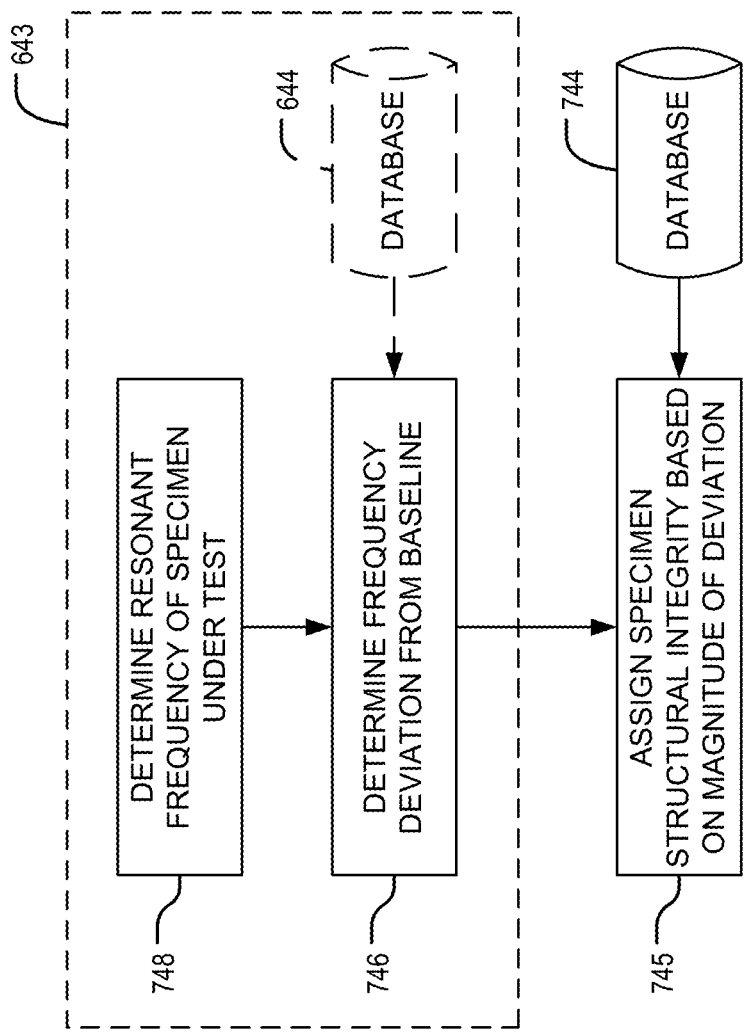
FIG. 7 is a flow diagram of a sub process of a sub process of a method for evaluating vibrational modes in cylindrical bodies, according to an exemplary embodiment of the present disclosure.

FIG. 7 provides a flow diagram of sub process 643 and step 645 of sub process 440, wherein the comparison is based on resonant frequency and the identified property of the specimen under test, or the identified structural quality of the specimen under test, is a structural integrity thereof.

For instance, at step 748 of sub process 643, a resonant frequency of the ovaling mode can be determined for the specimen under test. The resonant frequency may be identified as a frequency of the frequency response curve having maximum amplitude. At step 746 of sub process 643, a frequency deviation from a reference resonant frequency may be determined. To this end, a reference resonant frequency may be similarly determined from a frequency response curve of the reference element obtained at step 644. The reference resonant frequency can be used as a baseline from which a deviation of the resonant frequency of the specimen under test can be determined.

In an embodiment, the deviation can be represented as a relative magnitude of the resonant frequency of the specimen under test compared to the reference resonant frequency. In an example, the relative magnitude of the specimen under test and the reference resonant frequency may indicate the structural integrity of the specimen under test to be at 80% of the structural integrity of the reference element, reflecting a decrease in the soundness of the material.

At step 745 of sub process 440, the frequency deviation determined at sub process 643 can be contextualized according to varying levels of structural integrity informed by data from a reference database 744. For instance, considered on a graded scale, a 5% deviation from a reference resonant frequency may be assigned a green color indicating a sound material, a 10% deviation from the reference resonant frequency may be assigned a yellow color indicating an acceptable material, a 15% deviation from the reference resonant frequency may be assigned an orange color indicating a questionable material, and a 20% deviation from the reference resonant frequency may be assigned a red color indicating an unsound material. In the example wherein the specimen under test is determined to be at 80% of the structural integrity of the reference element, it can be determined at step 745 of sub process 440 that the specimen under test is "red" and, accordingly, of unfit soundness for use.

Figure 8:
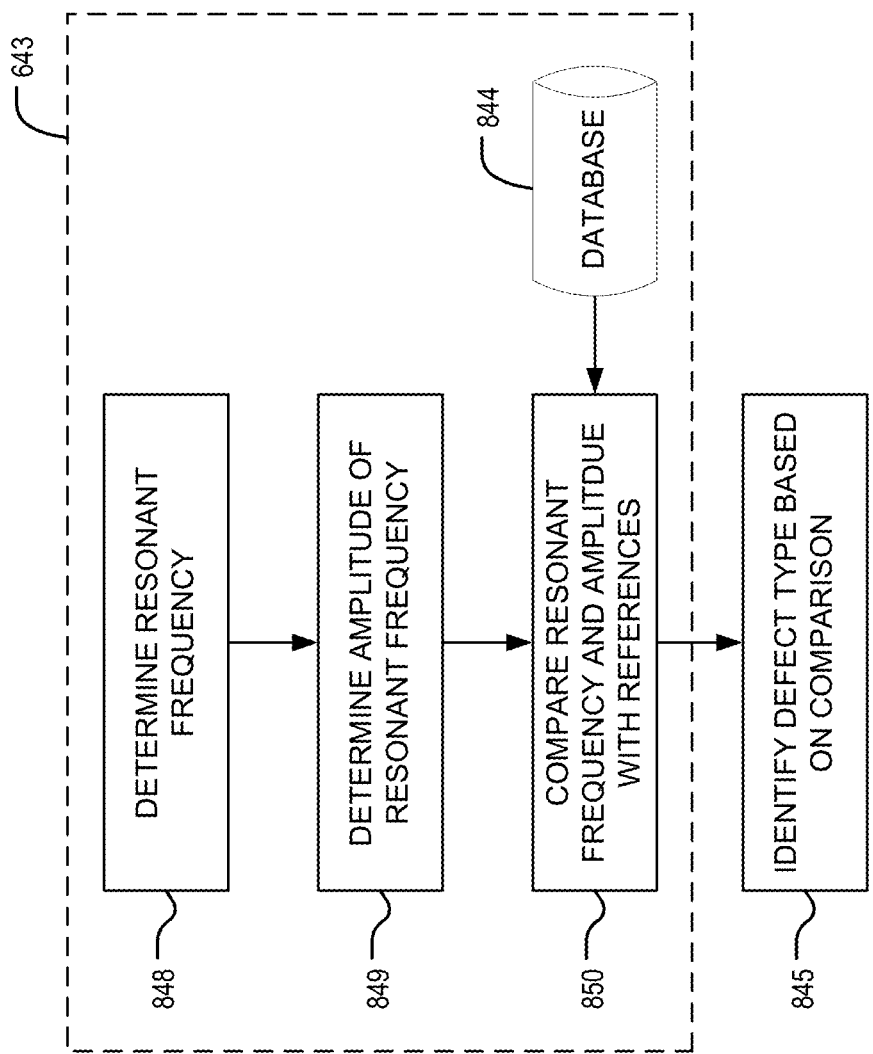
FIG. 8 is a flow diagram of a sub process of a sub process of a method for evaluating vibrational modes in cylindrical bodies, according to an exemplary embodiment of the present disclosure.

FIG. 8 provides a flow diagram of sub process 643 and step 645 of sub process 440, wherein the comparison is based on resonant frequency, amplitude of the resonant frequency, and the identified property of the specimen under test, or the identified structural quality of the specimen under test, is a defect type thereof.

For instance, at step 848 of sub process 643, a resonant frequency of the ovaling mode can be determined for the specimen under test. The resonant frequency may be identified as a frequency of the frequency response curve having maximum amplitude. At step 849 of sub process 643, an amplitude of the resonant frequency can be determined.

At step 850 of sub process 643, one or more reference elements within a reference database 844 can be determined and used for comparison. As describe above, the one or more reference elements within the reference database may be reference elements having a similar material type and size but with varying conditions or associated defect types, including "healthy" conditions. Frequency response curves associated with each of the one or more reference elements may have corresponding resonant frequencies and amplitudes thereof. Accordingly, at step 850 of sub process 643, the resonant frequency determined at step 848 of sub process 643 and the amplitude of the resonant frequency determined at step 849 of sub process 643 may be compared to corresponding values of the one or more reference elements obtained from the reference database 844.

In this way, according to an embodiment, correlations between the frequency response of the specimen under test and frequency responses of the one or more reference elements can be evaluated at step 845 of sub process 440 to determine a likely defect type of the specimen under test.

As described above, identifiable defect types of the specimen under test can include knots and cross-grain for wood, voids, delamination and external agents in concrete and steel as well as imperfections that manifest as a result of poor processing of the material or defective operation during its manufacturing, including casting, filling, tempering, and cooling.

In an embodiment, the specimen under test may be wood and may be identified as having a resonant frequency, and an amplitude thereof, that are highly correlated with corresponding values of a wood reference element that is healthy, or of sounds structural quality. Accordingly, at step 845 of sub process 440, the specimen under test may be identified as healthy or sound. In another embodiment, the specimen under test may be steel and may be identified as having a resonant frequency and amplitude highly correlated with corresponding values of a steel reference element that is corroded. Accordingly, at step 845 of sub process 440, the specimen under test may be identified as corroded.

According to an embodiment, identification of a defect type within a specimen under test may inform decisions regarding the structural quality thereof. For instance, assuming the specimen under test is wood, the resonant frequency of the wood may only indicate, as determined in FIG. 7, an 8% deviation from baseline. Considered together with the amplitude of the resonant frequency, however, as in FIG. 8, it may be determined that the wood is deteriorated by termites and, thus, an 8% deviation from baseline should be considered as more concerning that the 'acceptable' grade assigned at step 745 of sub process 440.

Moreover, identification of a defect type may indicate a practicality of corrective measures for the specimen under test. For instance, assuming the specimen under test is a steel cylinder, a hairline fracture in the steel cylinder may be correctable while a different type of fracture in the steel cylinder may indicate that the steel cylinder needs to be replaced.

EXAMPLES

Figure 9:
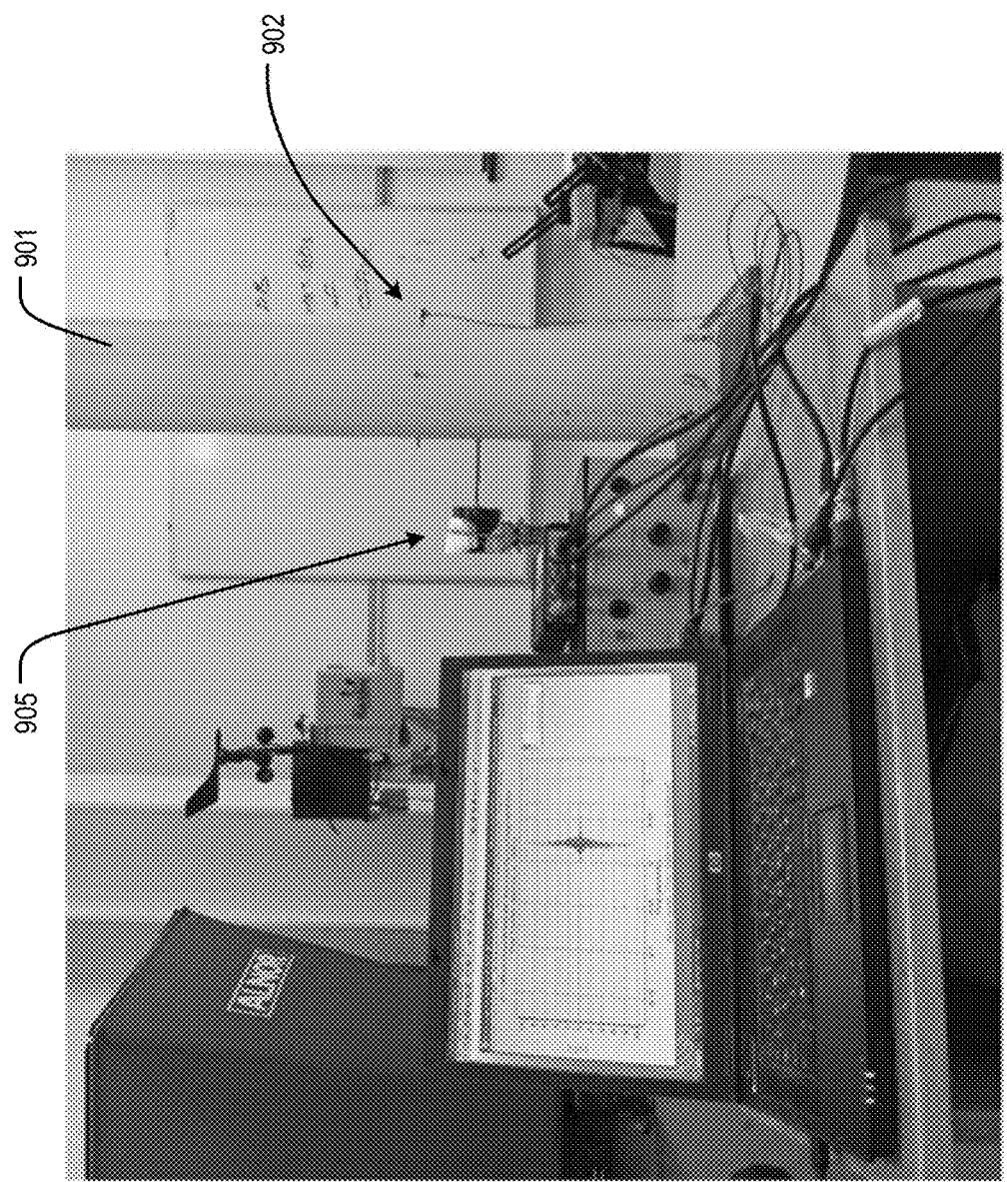
FIG. 9 is an illustration of an experimental setup of a system employing a method for generating, measuring, and evaluating vibrational modes in cylindrical bodies, according to an exemplary embodiment of the present disclosure.
Figure 10:
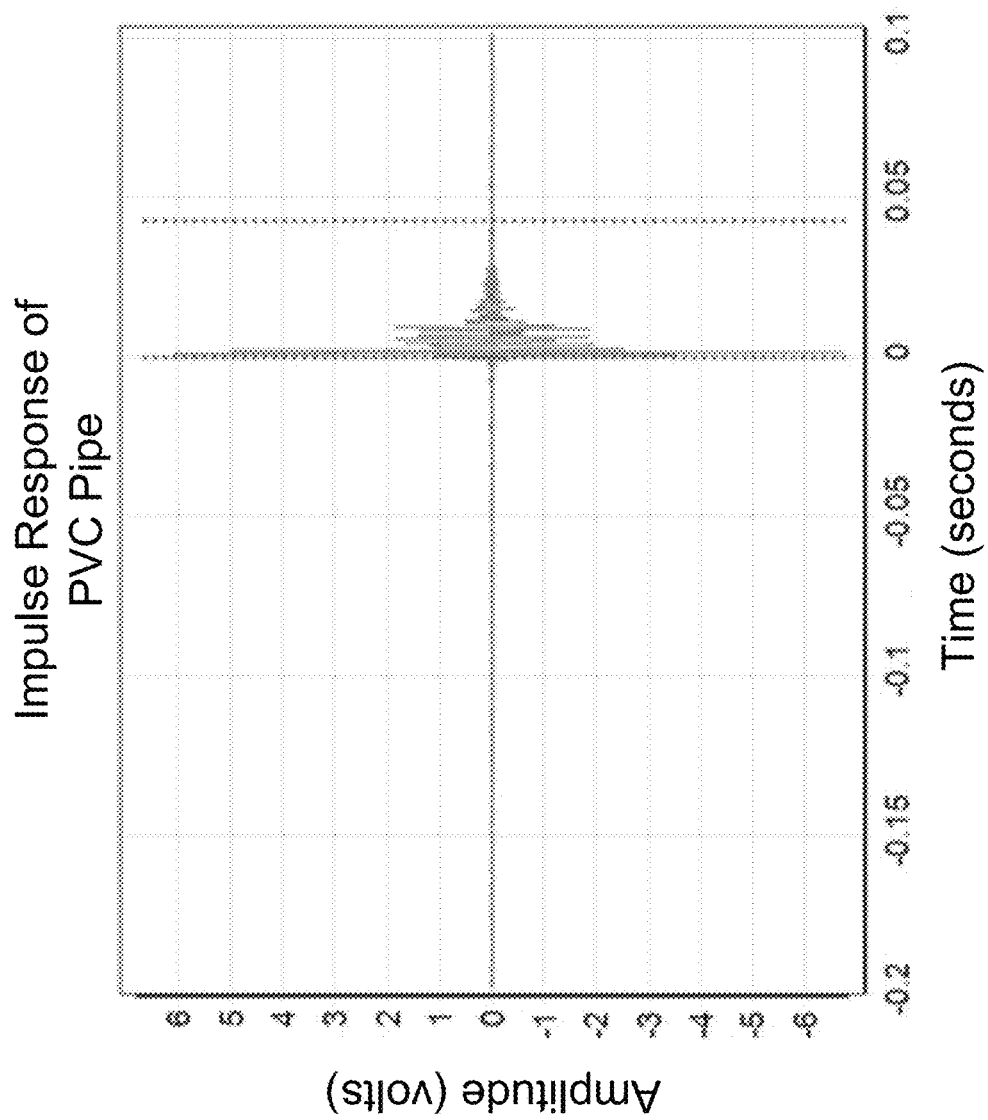
FIG. 10 is a graphical illustration of data acquired during evaluation of a vibrational modes in cylindrical bodies, according to an exemplary embodiment of the present disclosure.
Figure 11:
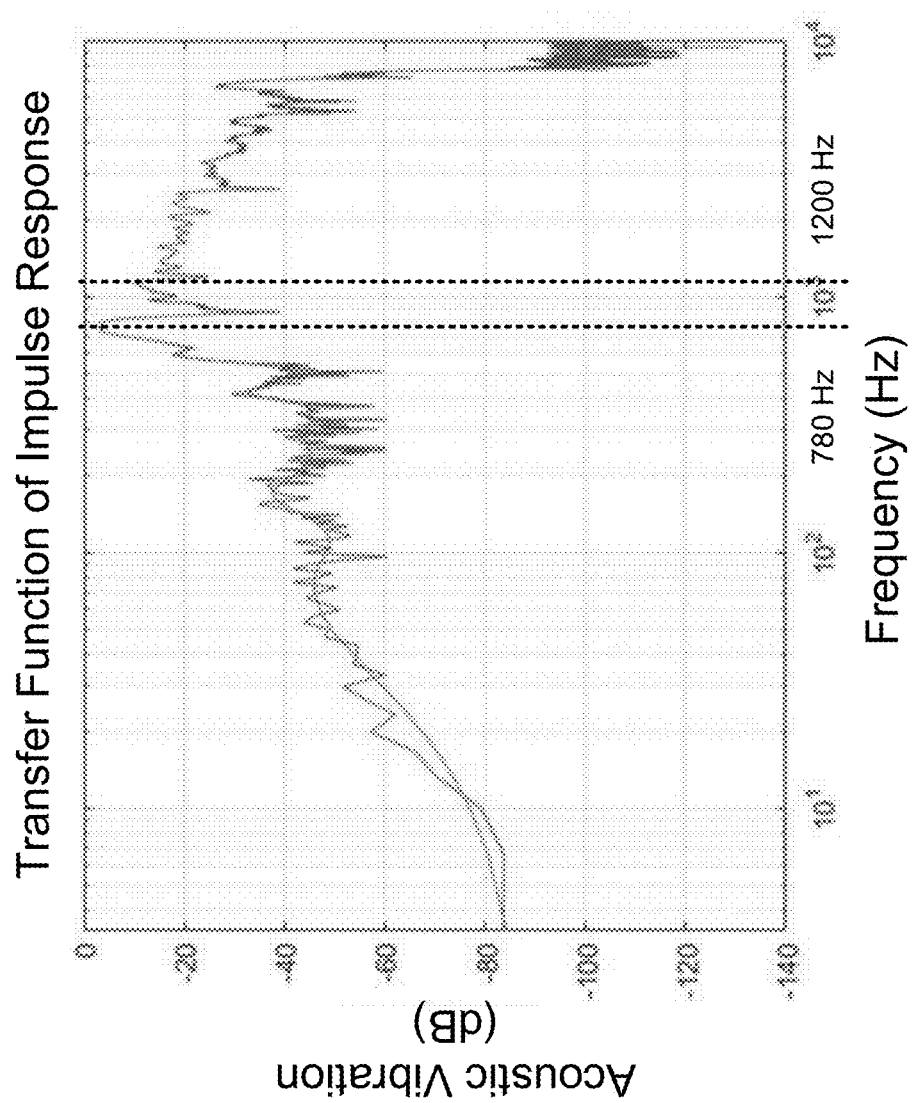
FIG. 11 is a graphical illustration of data acquired during evaluation of a vibrational modes in cylindrical bodies, according to an exemplary embodiment of the present disclosure.

With reference now to FIG. 9 through FIG. 11, aspects of the above described methods will be implemented within a laboratory environment.

Experimental tests were carried out on a circular hollow polyvinyl chloride (PVC) pipe 901 as the specimen under test with an external diameter of 168 mm and a thickness of 5.0 mm. As shown in FIG. 9, an electro-dynamic shaker 905 (i.e. signal generator) was used as a source of vibrations for exciting the specimen under test. Regarding the electro-dynamic shaker 905, an end of an associated rod (e.g. a "stinger") was firmly screwed to the vibrating base of the electro-dynamic shaker 905 while the other end of the associated rod was attached via nuts to the PVC pipe 901. In an non-limiting, the excitatory stimulus may be applied by an exciter type 5961 manufactured by Bruel & Kjaer. (See "Hand-held Exciter-Type 5961", Bruel & Kjaer North America Inc. (HQ), 3079 Premiere Parkway, Suite 120, Duluth, Ga. 30097, U.S.A.). The shaker 905 was attached on a cross-sectional plane normal to axis of the PVC pipe 901 such that the motion of shaft of the electro-dynamic shaker 905 was oriented radially. A measuring signal transducer 902, a piezoelectric accelerometer of type 4371, was attached to the PVC pipe 901 successively at four positions one quarter of the cylinder circumference apart beginning from a position right above the rod of the electro-dynamic shaker 905, as shown in FIG. 9.

The excitation signal used for measurements was a sinusoidal sweep with gradually increasing frequency in the frequency range between 10 Hz and 15 KHz. A vibratory response of the PVC pipe 901, or impulse response thereof, was acquired through an automatic procedure inbuilt in an ODEON® room acoustical simulation and measurement software (i.e., Odeon Combined 14, v4 including incorporated measurement functionality, Odeon 14 Features, Odeon A/S, DTU Science Park, Diplomvej Bldg. 381, DK-2800 Kgs. Lyngby Denmark https://odeon.dk/whats-new-version-14/, incorporated herein by reference in its entirety). Therefore, the impulse response is processed through performing a cross-correlation operation between the response of the test specimen and the excitation signal causing this response.

In the frequency domain, the transfer function, resulting from performing a Fourier transform on the impulse response was accomplished through the FFT algorithm.

According to an embodiment, FIG. 10 shows a plot of the impulse response resulting from a measurement on the PVC pipe. The y-axis shows the amplitude on a linear scale with arbitrary units. As can be seen from the plot, the response signals start a short time after t=0, with the first harmonic showing at approximately t=0.005 seconds. The second harmonic, the ovaling mode, shows at about t=0.01 seconds with an amplitude of about 4. This plot does not show the ovaling mode clearly enough to calculate the ovaling frequency.

After applying a Fourier transform to the impulse response of FIG. 10 via FFT, for instance, the resultant transfer function in the frequency domain may be visualized as in FIG. 11. FIG. 11 displays two curves wherein one is an approximation of the other and conveys the same information. The curves indicate maximal amplitude at −780 Hz, which corresponds to the resonant frequency of the ovaling mode. Another peak at 1200 Hz is that of the next even extensional mode. However, the ovaling mode exhibits its peak clearly, and exceeds the level of other peaks by more than 10 dB. For a very thin cylindrical shell, the ovaling mode exhibits its presence for an excitation at a frequency such that the circumference of the shell corresponds to approximately two bending wavelengths while for the next even cross-sectional mode the circumference corresponds to four wavelengths, i.e. at a frequency double of that of ovaling mode. This relationship however becomes more complicated in the case of bending waves and for a thick cylinder.

A testing apparatus and method for non-destructive testing of elements of solid materials using mechanical vibrations is described. The apparatus does not use ultrasonic signals with the accompanying problems of attaching probes, nor does it use dangerous penetrating radiation that requires specialized cumbersome, heavy, sensitive, and costly equipment for generating hazardous rays. The testing method is based on principles that do not require either deep knowledge or special training from the operator, and uses equipment that is affordable and that is light in weight so that it can be borne by the operator for on-site testing. The measurement depends only on the cross-sectional size of the inspected element, which is easily obtained with a tape measure, and not on its axial extent.

The testing apparatus and method for testing may be applied to inspecting weight bearing elements of cylindrical shape that are used in construction or as parts of larger building structures, such as columns, pillars in harbor piers or for supporting bridges. In the wood industry, the test may be used for sorting logs according to their strength quality prior to cutting into lumber, identifying trees most likely to yield good quality lumber or those that are infected with insects or disease, with a goal towards treating or isolating the damaged tree. For wooden poles, such as those which bear telephone or electrical cables, the test may be applied to identify those poles which need replacement.

The experimental testing of the present disclosure proves that is usable for in-situ testing and field measurements. A testing product may include a pair of identical hammer-like tools that each generate a stress wave in the cylinder and which are steered to operate simultaneously, which is achieved through a latching system for triggering the motion of the two hammers simultaneously. Depending on the strength of the material and the size of the cylindrical element, the contact surfaces of the hammer tips and the points of application of the blow are preferably tailored to the test object. Thus, cylinders of larger diameter and/or softer materials may use softer contacts than thinner and/or harder materials.

Figure 12:
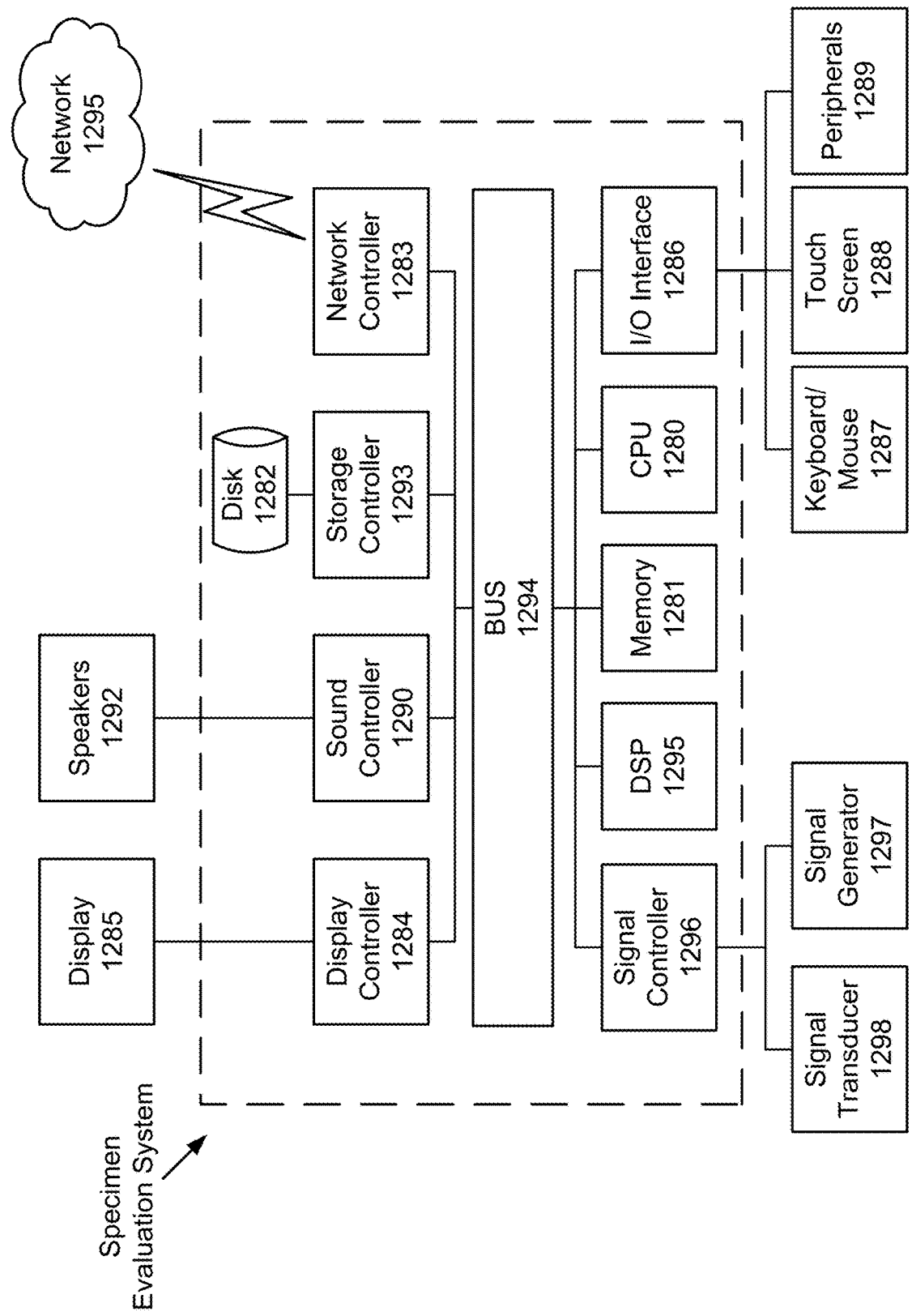
FIG. 12 is a non-limiting schematic of a hardware configuration of a computing environment for generating, measuring, and evaluating vibrational modes in cylindrical bodies, according to an exemplary embodiment of the present disclosure.

Next, a hardware description of the specimen evaluation system according to exemplary embodiments is described with reference to FIG. 12. In FIG. 12, the specimen evaluation system includes a CPU 1280 which performs the processes described above/below. The process data and instructions may be stored in memory 1281. These processes and instructions may also be stored on a storage medium disk 1282 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the specimen evaluation system communicates, such as a server or computer.

Further, the claimed advancements may be provided as a utility application, background daemon, or component of an operating system, or combination thereof, executing in conjunction with CPU 1280 and an operating system such as Microsoft Windows 7, UNIX, Solaris, LINUX, Apple MAC-OS and other systems known to those skilled in the art.

The hardware elements in order to achieve the specimen evaluation system may be realized by various circuitry elements, known to those skilled in the art. For example, CPU 1280 may be a Xenon or Core processor from Intel of America or an Opteron processor from AMD of America, or may be other processor types that would be recognized by one of ordinary skill in the art. Alternatively, the CPU 1280 may be implemented on an FPGA, ASIC, PLD or using discrete logic circuits, as one of ordinary skill in the art would recognize. Further, CPU 1280 may be implemented as multiple processors cooperatively working in parallel to perform the instructions of the inventive processes described above.

The specimen evaluation system in FIG. 12 also includes a network controller 1283, such as an Intel Ethernet PRO network interface card from Intel Corporation of America, for interfacing with network 1295. As can be appreciated, the network 1295 can be a public network, such as the Internet, or a private network such as an LAN or WAN network, or any combination thereof and can also include PSTN or ISDN sub-networks. The network 1295 can also be wired, such as an Ethernet network, or can be wireless such as a cellular network including EDGE, 3G and 4G wireless cellular systems. The wireless network can also be WiFi, Bluetooth, or any other wireless form of communication that is known.

The specimen evaluation system further includes a display controller 1284, such as a NVIDIA GeForce GTX or Quadro graphics adaptor from NVIDIA Corporation of America for interfacing with display 1285, such as a Hewlett Packard HPL2445w LCD monitor. A general purpose I/O interface 1286 interfaces with a keyboard and/or mouse 1287 as well as a touch screen panel 1288 on or separate from display 1285. General purpose I/O interface also connects to a variety of peripherals 1289 including printers and scanners, such as an OfficeJet or DeskJet from Hewlett Packard. In a non-limiting example of the methods described herein, an operator may input, through the I/O interface 1286 via the keyboard/mouse 1287, touch screen 1288, or peripherals 1289, parameters of the specimen under test. The parameters of the specimen under test may include, as described above, diameter, material composition, humidity, visible degradation, location, and the like. The parameters of the specimen under test may be stored in the memory 1281 or in the storage disk 1282.

According to an embodiment, the specimen evaluation system includes a sound controller 1290 is also provided in the specimen evaluation system, such as Sound Blaster X-Fi Titanium from Creative, to interface with speakers/microphone 1292 thereby providing sounds and/or music.

According to an embodiment, the hardware elements of the specimen evaluation system may include processing circuitry (e.g., CPU 1280) which can include without limitation one or more processors, one or more special-purpose processors (such as digital signal processing (DSP) chips, graphics acceleration processors, application specific integrated circuits (ASICs), and/or the like), and/or other processing structure or means. The above-described processors can be specially-programmed to perform operations including, among others, fast Fourier transforms, analog to digital conversions, frequency analyses, and the like. Some embodiments may have a separate DSP 1295, depending on desired functionality.

According to an embodiment, the specimen evaluation system may include a signal controller 1296 configured to control signal generator(s) 1297 and/or signal transducer(s) 1298 of the specimen evaluation system. In one instance, the signal controller 1296 controls generation of a signal for probing a cross-sectional area of a specimen under test. In another instance, the signal controller 1296 controls transduction of signals received at one or more signal transducers. In an embodiment, these instances may exists independently or interpedently according to specifics of an individual test.

The general purpose storage controller 1293 connects the storage medium disk 1282 with communication bus 1294, which may be an ISA, EISA, VESA, PCI, or similar, for interconnecting all of the components of the specimen evaluation system. A description of the general features and functionality of the display 1285, keyboard and/or mouse 1287, as well as the display controller 1284, storage controller 1293, network controller 1283, sound controller 1290, and general purpose I/O interface 1286 is omitted herein for brevity as these features are known.

This invention is of a particularly appropriate use in the inspection corrosion in reinforced concrete construction columns, bridge or pier pillars, and for investigating the extent of rot attack in wooden poles used for bearing telephone or electricity cables, logs or trunks hosted in logs, wood poles, and in standing trees. It is in general of extended application to cylindrically shaped construction elements made of solid materials, these elements may be solid or hollow.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for determining a structural quality of a cylindrical element, comprising:
   measuring, by processing circuitry and as a result of a single applied force, surface vibrations of the cylindrical element via four or more surface transducers arranged on the cylindrical element along a circumference of the cylindrical element, the four or more surface transducers being equally spaced along the circumference of the cylindrical element;
   processing, by the processing circuitry, digital signals corresponding to each of the four or more surface transducers in order to generate a composite digital signal;
   transforming, by the processing circuitry, the composite digital signal to a frequency domain;
   comparing, by the processing circuitry, the transformed composite digital signal to a reference composite digital signal; and
   determining, by the processing circuitry and based on the comparing, the structural quality of the cylindrical element.

2. The method of claim 1, wherein a first surface transducer of the four or more surface transducers and a third surface transducer of the four or more surface transducers are diametrically opposed, a second surface transducer of the four or more surface transducers and a fourth surface transducer of the four or more surface transducers are diametrically opposed, and the processing processes the digital signals by
   generating a first paired digital signal via addition of a first digital signal from the first surface transducer and a third digital signal from the third surface transducer,
   generating a second paired digital signal via addition of a second digital signal from the second surface transducer and a fourth digital signal from the fourth surface transducer, and
   generating the composite digital signal via subtraction of the second paired digital signal from the first paired digital signal.

3. The method of claim 1, further comprising
   isolating, by the processing circuitry, an ovaling mode within the transformed composite digital signal, wherein
   the comparing compares the isolated ovaling mode within the transformed composite digital signal to a reference ovaling mode within the reference composite digital signal.

4. The method of claim 3, further comprising:
   rating the structural quality of the cylindrical element based on a deviation of a frequency of the isolated ovaling mode within the transformed composite digital signal from a reference frequency of the reference ovaling mode within the reference composite digital signal, and the comparing compares the frequency of the isolated ovaling mode within the transformed composite digital signal to the reference frequency of the reference ovaling mode within the reference composite digital signal to determine the deviation.

5. The method of claim 3, wherein the comparing compares a frequency of the isolated ovaling mode within the transformed composite digital signal to a reference frequency of the reference ovaling mode within the reference composite digital signal.

6. The method of claim 5, wherein
   the comparing compares an amplitude of the isolated ovaling mode within the transformed composite digital signal to a reference amplitude of the reference ovaling mode within the reference composite digital signal and
   the determining determines, as the structural quality of the cylindrical element, a defect type, the defect type being one of a plurality of defect types associated with each of a plurality of reference composite digital signals and being based on
   the comparison of the frequency of the isolated ovaling mode within the transformed composite digital signal to the reference frequency of the reference ovaling mode within the reference composite digital signal and
   the comparison of the amplitude of the isolated ovaling mode within the transformed composite digital signal to the reference amplitude of the reference ovaling mode within the reference composite digital signal.

7. The method of claim 1, further comprising
   acquiring, by the processing circuitry, parameters of the cylindrical element including a type of the cylindrical element and a diameter of the cylindrical element, wherein the reference composite digital signal is one of a plurality of reference composite digital signals associated, in a database, with the type of the cylindrical element and the diameter of the cylindrical element.

8. The method of 1, wherein the single applied force generates ovaling vibrations.

9. An apparatus for determining a structural quality of a cylindrical element, comprising:
   processing circuitry configured to
   measure, as a result of a single applied force, surface vibrations of the cylindrical element via four or more surface transducers arranged on the cylindrical element along a circumference of the cylindrical element, the four or more surface transducers being equally spaced along the circumference of the cylindrical element,
   process digital signals corresponding to each of the four or more surface transducers in order to generate a composite digital signal,
   transform the composite digital signal to a frequency domain,
   compare the transformed composite digital signal to a reference composite digital signal, and
   determine, based on the comparing, the structural quality of the cylindrical element.

10. The apparatus of claim 9, wherein a first surface transducer and a third surface transducer are diametrically opposed, a second surface transducer and a fourth surface transducer are diametrically opposed, and the processing circuitry is configured to
generate a first paired digital signal via addition of a first digital signal from the first surface transducer and a third digital signal from the third surface transducer,
generate a second paired digital signal via addition of a second digital signal from the second surface transducer and a fourth digital signal from the fourth surface transducer, and
generate the composite digital signal via subtraction of the second paired digital signal from the first paired digital signal.

11. The apparatus of claim 9, wherein the processing circuitry is further configured to
isolate an ovaling mode within the transformed composite digital signal, and
compare the transformed composite digital signal to a reference composite digital signal by comparing the isolated ovaling mode within the transformed composite digital signal to a reference ovaling mode within the reference composite digital signal.

12. The apparatus of claim 11, wherein the structural quality of the cylindrical element is a rating based on a deviation of a frequency of the isolated ovaling mode within the transformed composite digital signal from a reference frequency of the reference ovaling mode within the reference composite digital signal, and the processing circuitry is further configured to
compare the frequency of the isolated ovaling mode within the transformed composite digital signal to the reference frequency of the reference ovaling mode within the reference composite digital signal to determine the deviation.

13. The apparatus of claim 11, wherein the processing circuitry is further configured to compare the transformed composite digital signal to a reference composite digital signal by comparing a frequency of the isolated ovaling mode within the transformed composite digital signal to a reference frequency of the reference ovaling mode within the reference composite digital signal.

14. The apparatus of claim 13, wherein the processing circuitry is further configured to
compare the transformed composite digital signal to a reference composite digital signal by comparing an amplitude of the isolated ovaling mode within the transformed composite digital signal to a reference amplitude of the reference ovaling mode within the reference composite digital signal, and
determine the structural quality of the cylindrical element by determining a defect type, the defect type being one of a plurality of defect types associated with each of a plurality of reference composite digital signals and being based on
the comparison of the frequency of the isolated ovaling mode within the transformed composite digital signal to the reference frequency of the reference ovaling mode within the reference composite digital signal and
the comparison of the amplitude of the isolated ovaling mode within the transformed composite digital signal to the reference amplitude of the reference ovaling mode within the reference composite digital signal.

15. A non-transitory computer-readable storage medium storing computer-readable instructions that, when executed by a computer, cause the computer to perform a method for determining a structural quality of a cylindrical element, comprising:
measuring, as a result of a single applied force, surface vibrations of the cylindrical element via four or more surface transducers arranged on the cylindrical element along a circumference of the cylindrical element, the four or more surface transducers being equally spaced along the circumference of the cylindrical element;
processing digital signals corresponding to each of the four or more surface transducers in order to generate a composite digital signal;
transforming the composite digital signal to a frequency domain;
comparing the transformed composite digital signal to a reference composite digital signal; and
determining, based on the comparing, the structural quality of the cylindrical element.

16. The non-transitory computer-readable storage medium of claim 15, wherein a first surface transducer and a third surface transducer are diametrically opposed, a second surface transducer and a fourth surface transducer are diametrically opposed, and the processing processes the digital signals by
generating a first paired digital signal via addition of a first digital signal from the first surface transducer and a third digital signal from the third surface transducer,
generating a second paired digital signal via addition of a second digital signal from the second surface transducer and a fourth digital signal from the fourth surface transducer, and
generating the composite digital signal via subtraction of the second paired digital signal from the first paired digital signal.

17. The non-transitory computer-readable storage medium of claim 15, further comprising
isolating an ovaling mode within the transformed composite digital signal, wherein
the comparing compares the isolated ovaling mode within the transformed composite digital signal to a reference ovaling mode within the reference composite digital signal.

18. The non-transitory computer-readable storage medium of claim 17, wherein the comparing compares a frequency of the isolated ovaling mode within the transformed composite digital signal to a reference frequency of the reference ovaling mode within the reference composite digital signal, and further comprising
rating the structural quality of the cylindrical element based on a deviation of the frequency of the isolated ovaling mode within the transformed composite digital signal from the reference frequency of the reference ovaling mode within the reference composite digital signal.

19. The non-transitory computer-readable storage medium of claim 17, wherein the comparing compares a frequency of the isolated ovaling mode within the transformed composite digital signal to a reference frequency of the reference ovaling mode within the reference composite digital signal.

20. The non-transitory computer-readable storage medium of claim 19, wherein
the comparing compares an amplitude of the isolated ovaling mode within the transformed composite digital signal to a reference amplitude of the reference ovaling mode within the reference composite digital signal and the determining determines, as the structural quality of the cylindrical element, a defect type, the defect type being one of a plurality of defect types associated with each of a plurality of reference composite digital signals and being based on the comparison of the frequency of the isolated ovaling mode within the transformed composite digital signal to the reference frequency of the reference ovaling mode within the reference composite digital signal and the comparison of the amplitude of the isolated ovaling mode within the transformed composite digital signal to the reference amplitude of the reference ovaling mode within the reference composite digital signal.

* * * * *